(12) United States Patent
Shiibashi

(10) Patent No.: US 11,107,590 B2
(45) Date of Patent: Aug. 31, 2021

(54) CLOUD-TO-LOCAL, LOCAL-TO-CLOUD SWITCHING AND SYNCHRONIZATION OF MEDICAL IMAGES AND DATA WITH ADVANCED DATA RETRIEVAL

(71) Applicant: Konica Minolta Healthcare Americas, Inc., Wayne, NJ (US)

(72) Inventor: Takao Shiibashi, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 323 days.

(21) Appl. No.: 15/940,781

(22) Filed: Mar. 29, 2018

(65) Prior Publication Data

US 2019/0304610 A1    Oct. 3, 2019

(51) Int. Cl.
| | |
|---|---|
| *G06Q 50/20* | (2012.01) |
| *G16H 80/00* | (2018.01) |
| *G16H 10/60* | (2018.01) |
| *G16H 30/20* | (2018.01) |
| *G06F 16/27* | (2019.01) |

(52) U.S. Cl.
CPC ............ *G16H 80/00* (2018.01); *G06F 16/27* (2019.01); *G16H 10/60* (2018.01); *G16H 30/20* (2018.01)

(58) Field of Classification Search
None
See application file for complete search history.

(56) References Cited

U.S. PATENT DOCUMENTS

| | | | |
|---|---|---|---|
| 2004/0249806 A1* | 12/2004 | Kanada | G06F 16/51 |
| 2008/0140723 A1* | 6/2008 | Hernandez | G16H 30/40 |
| 2009/0136105 A1* | 5/2009 | Hollebeek | G06F 19/321 |
| | | | 382/128 |
| 2010/0010983 A1* | 1/2010 | Crucs | G06F 19/321 |
| | | | 707/E17.005 |
| 2011/0110568 A1* | 5/2011 | Vesper | G06Q 10/10 |
| | | | 382/128 |
| 2012/0070045 A1* | 3/2012 | Vesper | G06Q 10/10 |
| | | | 382/128 |
| 2012/0265551 A1* | 10/2012 | Backhaus | G06F 19/321 |
| | | | 705/2 |

(Continued)

*Primary Examiner* — Jonathan Ng
(74) *Attorney, Agent, or Firm* — Osha Bergman Watanabe & Burton LLP

(57) ABSTRACT

A method is provided for advanced-retrieval of medical data in a system that synchronizes medical data between a cloud repository on a cloud server and a plurality of local repositories on a plurality of local servers of healthcare facilities connected to the cloud server. The method is executed by the cloud server and includes: receiving diagnostic reservation information, that includes timing information for a future diagnosis date and diagnosis information that associates the diagnostic reservation information with a medical image stored in the cloud server; receiving an advanced-retrieval request that comprises an advanced-retrieval time period; determining, in response to receiving the advanced-retrieval request, that the timing information of the diagnostic reservation information overlaps with the advanced-acquisition time period; transmitting in response to the medical image being associated with the diagnostic reservation information, the medical images and data.

20 Claims, 15 Drawing Sheets

(56) References Cited

U.S. PATENT DOCUMENTS

| | | | | |
|---|---|---|---|---|
| 2014/0142984 A1* | 5/2014 | Wright | ................ | G06F 21/6245 |
| | | | | 705/3 |
| 2014/0153808 A1* | 6/2014 | Wu | ....................... | G06T 7/0012 |
| | | | | 382/131 |
| 2015/0127379 A1* | 5/2015 | Sorenson | ............... | G16H 10/20 |
| | | | | 705/3 |

* cited by examiner

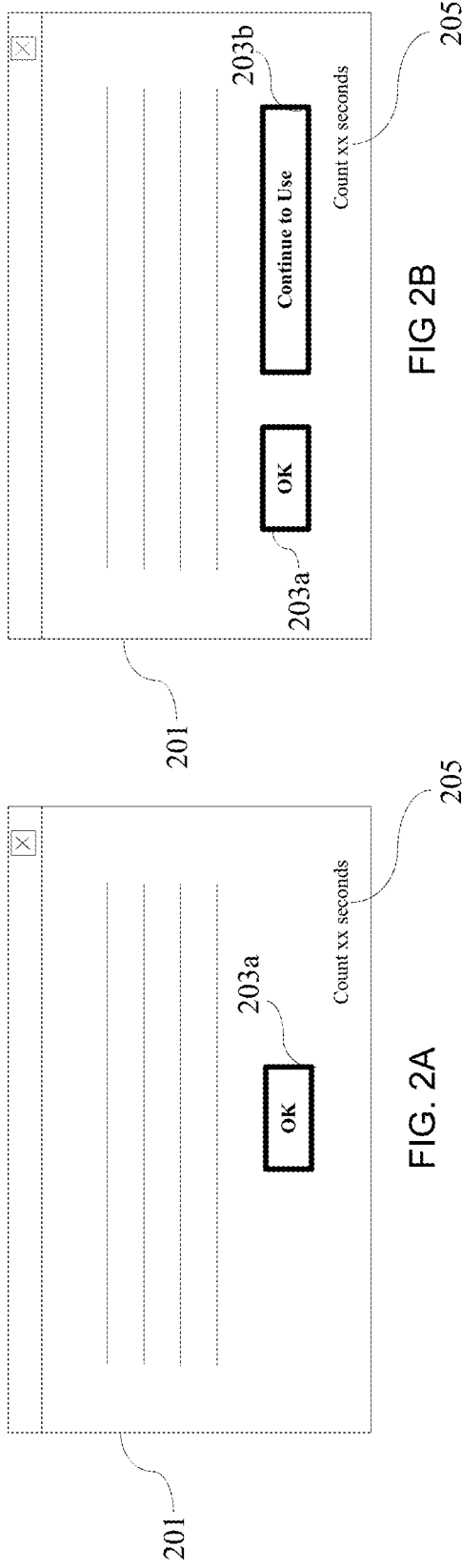

CLOUD-TO-LOCAL, LOCAL-TO-CLOUD SWITCHING AND SYNCHRONIZATION OF MEDICAL IMAGES AND DATA WITH ADVANCED DATA RETRIEVAL

BACKGROUND

Medical images and medical data play a crucial role in the diagnosis of a patient. Healthcare facilities (e.g., hospitals) have realized the benefits of electronically storing medical images and medical data. The digitalization of the medical images and data not only enables users to easily access medical images and medical data, but also enables the images and data to be easily shared between multiple healthcare facilities.

In the healthcare industry, the use of a system known as a Picture Archiving and Communications System ("PACS") is becoming increasing popular for convenient storage and access of medical images. Generally, PACS comprises a multitude of devices working cooperatively to digitally capture, store, manage, distribute, and display medical images generated by various imaging modalities, such as computed tomography (CT), magnetic resonance imaging (MRI), position emission tomography (PET), ultrasound, X-ray, etc. PACS allows various healthcare facilities to share all types of images captured internally or externally.

More recently, cloud-based PACS have emerged as a way to improve efficiency and accessibility of traditional PACS. In general, a "cloud" can be understood as an online storage system that provides remote, on-demand access of computing resources and data over the Internet to multiple computers and devices in various locations. Cloud-based PACS may be provided by vendors who use remote or off-site data centers in various locations for storage of medical images.

SUMMARY

In general, in one aspect, the invention is related to a method for advanced-retrieval of medical data in a system that synchronizes medical data between a cloud repository on a cloud server and a plurality of local repositories on a plurality of local servers of healthcare facilities connected to the cloud server, wherein the healthcare facilities include at least a first healthcare facility including a first local repository and a second healthcare facility including a second local repository. The method comprising: receiving, by the cloud server and from the first healthcare facility, diagnostic reservation information, wherein the diagnostic reservation information comprises: timing information for a future diagnosis date, and diagnosis information that associates the diagnostic reservation information with a medical image stored in the cloud server; receiving, by the cloud server and from the second healthcare facility, an advanced-retrieval request that comprises an advanced-retrieval time period; determining, by the cloud server and in response to receiving the advanced-retrieval request, that the timing information of the diagnostic reservation information overlaps with the advanced-acquisition time period; transmitting, by the cloud server and to the second local repository in response to the medical image being associated with the diagnostic reservation information, the medical images and data.

In general, in one aspect, the invention is related to a non-transitory computer-readable medium (CRM) storing instructions that cause a cloud server coupled to a computer to perform an operation for advanced-retrieval of medical data in a system that synchronizes medical data between a cloud repository on the cloud server and a plurality of local repositories on a plurality of local servers of healthcare facilities connected to the cloud server, wherein the healthcare facilities include at least a first healthcare facility including a first local repository and a second healthcare facility including a second local repository. The operation comprising: receiving, by the cloud server and from the first healthcare facility, diagnostic reservation information, wherein the diagnostic reservation information comprises: timing information for a future diagnosis date, and diagnosis information that associates the diagnostic reservation information with a medical image stored in the cloud server; receiving, by the cloud server and from the second healthcare facility, an advanced-retrieval request that comprises an advanced-retrieval time period; determining, by the cloud server and in response to receiving the advanced-retrieval request, that the timing information of the diagnostic reservation information overlaps with the advanced-acquisition time period; transmitting, by the cloud server and to the second local repository in response to the medical image being associated with the diagnostic reservation information, the medical images and data.

In general, in one aspect, the invention is related to a system that synchronizes medical data. The system comprising: a cloud server; a cloud repository on the cloud server; and a plurality of local repositories on a plurality of local servers of healthcare facilities connected to the cloud server, wherein the healthcare facilities include at least a first healthcare facility including a first local repository and a second healthcare facility including a second local repository, and the cloud server: receives, from the first healthcare facility, diagnostic reservation information, wherein the diagnostic reservation information comprises: timing information for a future diagnosis date, and diagnosis information that associates the diagnostic reservation information with a medical image stored in the cloud server; receives, from the second healthcare facility, an advanced-retrieval request that comprises an advanced-retrieval time period; determines, in response to receiving the advanced-retrieval request, that the timing information of the diagnostic reservation information overlaps with the advanced-acquisition time period; transmits, to the second local repository in response to the medical image being associated with the diagnostic reservation information, the medical images and data.

Other aspects and advantages of the invention will be apparent from the following description and the appended claims.

BRIEF DESCRIPTION OF DRAWINGS

FIGS. 2A and 2B show a display message in accordance with one or more embodiments.

FIG. 3 shows a data table in accordance with one or more embodiments.

DETAILED DESCRIPTION

Figure 1A:
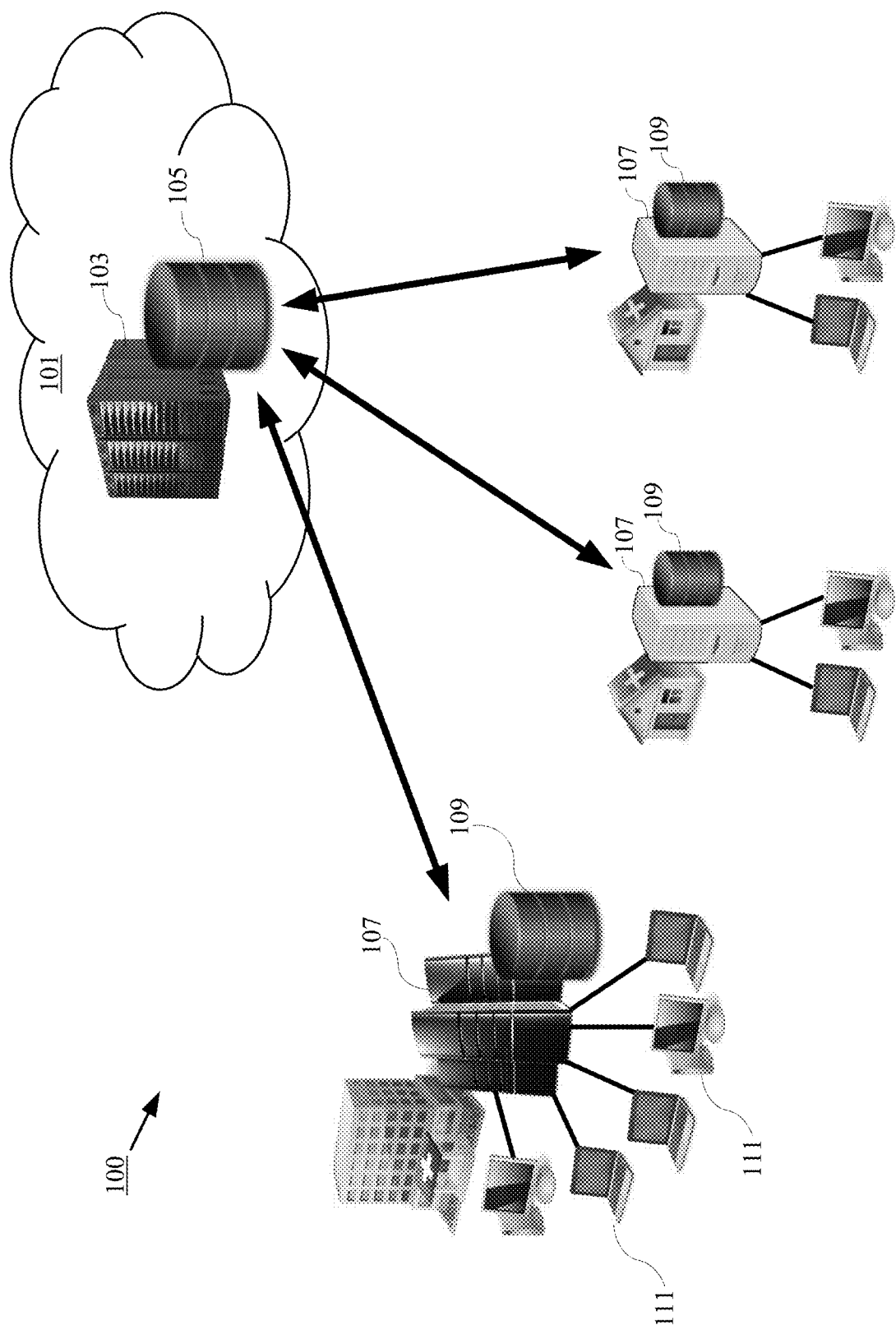
FIGS. 1A and 1B show a system in accordance with one or more embodiments.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In general, one or more embodiments of the invention provide a method, a non-transitory computer readable medium, and a system configured for cloud-to-local, local-to-cloud switching and synchronization of medical images and data (herein also referred to as just "medical images") with a mechanism for automatically retrieving (i.e., prefetching and/or advanced-retrieval) medical images and data prior to a patient's scheduled diagnosis. The cloud-based PACS in accordance with one or more embodiments enables all healthcare facilities that are given permission to access a cloud data repository or database ("cloud repository"), such as facilities within the same hospital group, to share medical images and data. The medical images and data may also include a patient's medical reports. For example, a healthcare facility would be able to access and retrieve its patients' medical images and data obtained at the other healthcare facilities that are "in-network" (i.e., having permission to access the same portion of the cloud repository). Specifically, according to one or more embodiments, in-network healthcare facilities can more effectively utilize cloud-based PACS to share and update medical images and data for patients who frequent more one or more of the in-network healthcare facilities.

Moreover, unlike conventional cloud-based PACS, one or more embodiments of the invention enable a healthcare facility that utilizes cloud-based PACS to remain operational even when a network connection between the healthcare facility and the cloud is disconnected. Specifically, in-network healthcare facilities that utilize one or more embodiments are able to automatically keep on-site or local data repositories or databases ("local repositories") on a local server updated with the most recent patient images and data stored in the cloud repository based on a need of the users of the cloud-based PACS (e.g., healthcare professionals). For example, if one facility updates or obtains a new medical image of a particular patient, the cloud repository may be automatically updated with the updated or new medical image, and all the local repositories of the in-network facilities that treat or care for that same patient may be automatically synchronized with the cloud repository.

In one or more embodiments, in the event of a loss of connection, the disconnected healthcare facilities automatically switch access to the local repositories instead of the cloud repository. This enables the healthcare facilities to establish a continuous workflow without experiencing any downtime caused by the disconnection from the network. Because the local repositories of in-network facilities are synchronized with the cloud repository, the facilities are able to at least temporarily access and work with the most up-to-date data, even without connection to the cloud. However, not all the data on the cloud repository need necessarily be synchronized. In one or more embodiments, the synchronization occurs only with respect to data that is necessary or is of interest to the respective facilities. For example, a facility may not want its local repository filled or local server burdened with medical images related to people who are not patients of that facility.

In one or more embodiments, when the connection is reestablished, the medical images and data stored in the local repositories during the time of network disconnection are automatically uploaded to the cloud repository. This enables all of the other in-network healthcare facilities to update their respective local repositories with the most up-to-date medical images and data.

In one or more embodiments, the cloud-based PACS is configured with a medical data advanced-retrieval function. Medical images and data stored in the cloud may be automatically retrieved by the local servers of healthcare facilities in advance of a patient's diagnosis. This enables the medical images and data to be retrieved before the patient arrives at a respective healthcare facility for a scheduled diagnosis, which prevents unnecessary delay in the diagnosis as a result of the amount of time required to retrieve the medical images and data from the cloud sever. For example, patient A receives a first diagnosis (i.e., a primary diagnosis)

at healthcare facility A. Patient A is then scheduled to have a follow-up diagnosis (i.e., a secondary diagnosis) at healthcare facility B. Prior to patient A arriving at healthcare facility B at the scheduled date and time of the follow-up diagnosis, Patient A's medical images and data taken at healthcare facility A may be readily available in the local systems of healthcare facility B for the physicians at healthcare facility B to perform an efficient diagnosis.

Figure 1B:
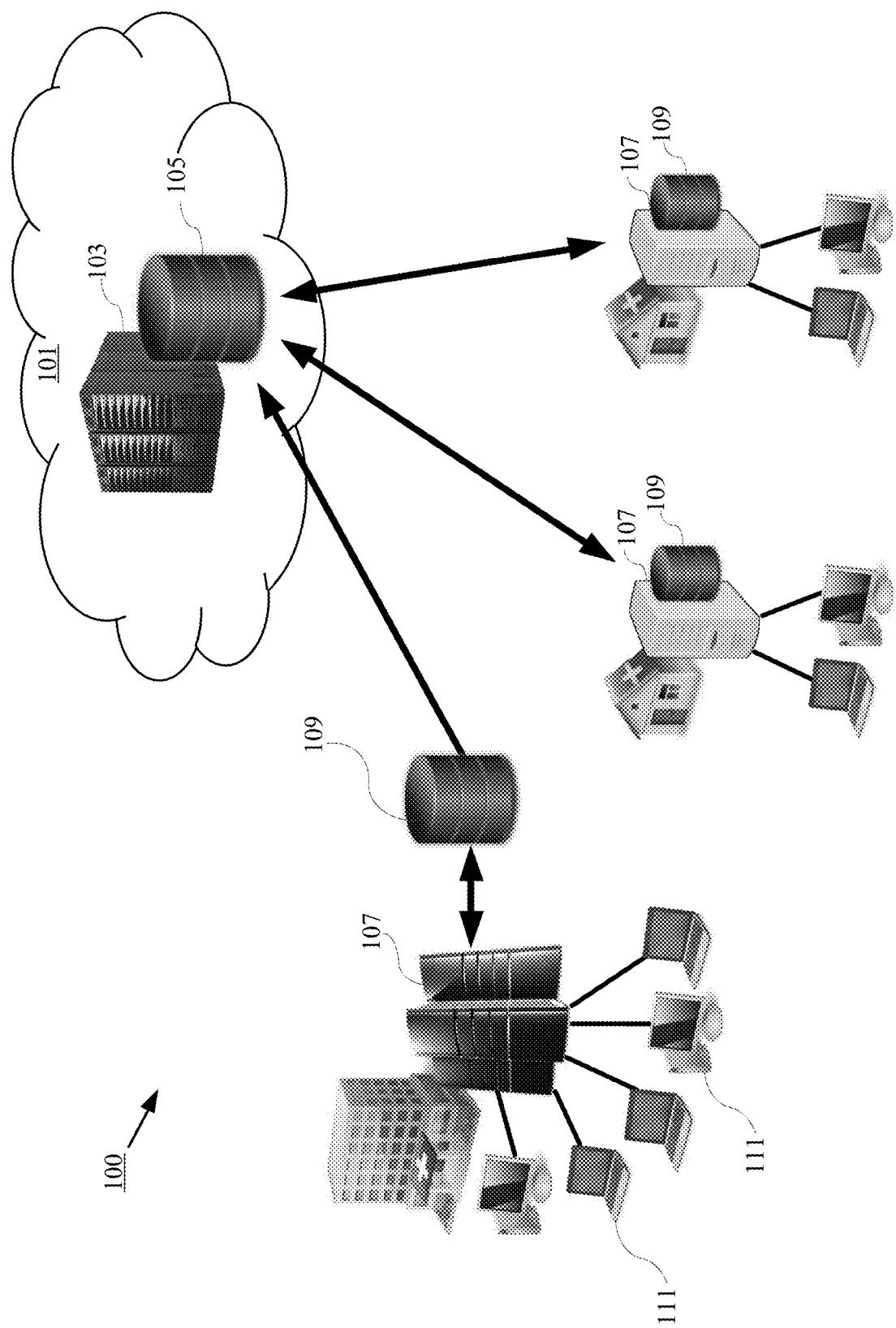

FIGS. 1A and 1B show a system (100) in accordance with one or more embodiments of the invention. As shown in FIGS. 1A and 1B, the system (100) includes a cloud (101) that includes a cloud server (103) with a cloud repository (105), and multiple local servers (107) (e.g., application proxy servers (APS)) and local repositories (109) associated with different in-network healthcare facilities (not labeled). The multiple local servers (107) are authorized to access/view the cloud server (103). In addition to the right to access the remote data on the cloud server (103), certain local servers (107) may also have the right to edit the remote data. Each of the healthcare facilities may be a type of facility that provides medical care such as a public hospital, a private hospital, a medical clinic, a dental clinic, etc.

As also shown in FIGS. 1A and 1B, each healthcare facility in the system (100) includes multiple user computing devices (111) (herein referred to as "a local computer") coupled to the local servers (107). Each local computer (111) may correspond to a personal computer (PC), a laptop, a mobile computing device (e.g., tablet PC, smartphone, etc.), a server, a mainframe, a kiosk, etc.

In one or more embodiments, the cloud server (103) with the cloud repository (105) may be operated by a vendor providing the cloud-based PACS or another third-party associated with such a vendor. In one or more embodiments, the cloud server (103) is a physical and/or virtual computing infrastructure that performs application and information processing. For example, the cloud server (103) may be a virtual server or a physical server accessed remotely via the Internet. In one or more embodiments, the cloud repository (105) is an online repository of data. For example, the cloud repository may be a virtual data room (VDR) or a database (or group of databases) accessed remotely via the Internet.

In one or more embodiments, the cloud server (103) is configured to receive the medical images and data transmitted from the local servers (107) and store the medical images and data in the cloud repository (105) as remote data.

In one or more embodiments, each local server (107) is operated by the associated healthcare facility. The local server (107) is configured to transmit the medical images and data received from the local computers (111) to the cloud repository (105) on the cloud server (103). Each local repository (109) is operated and maintained by the associated healthcare facility. The local repository (109) may locally store medical images and data received from the local server (107) and the cloud repository (105) local data.

In one or more embodiments, the local computers (111) are operated by medical professionals associated with the respective healthcare facilities and are configured to transmit to the local server (107) medical images and data taken from one or more modalities (not shown) in the healthcare facility. In one or more embodiments, the local computers (111) may be configured as the local server (107). In one or more embodiments, the local computers (111) may also include the local repository (109).

In one or more embodiments, the local computers are configured to store an application provided by the vendor that operates the cloud (101). In one or more embodiments, the application may be a medical synchronization application provided by a third-party associated with the vendor. The medical synchronization application may be an independent software application registered to the device (i.e., the cloud (101) or the local servers (107)) that the medical synchronization application is stored in or a web-browser based application with a graphical user interface ("GUI") that allows the local computers (111) to access the cloud (101) to synchronize medical data with the cloud (101). In one or more embodiments, the cloud server (103) and each of the local servers (107) may store a copy of the medical synchronization application in the respective repositories.

FIG. 1A shows an example in accordance with one or more embodiments where the connection between the in-network healthcare facilities and the cloud (101) is stable. In this state, the multiple in-network healthcare facilities may communicate bilaterally with the cloud (101). As shown in FIG. 1A, the in-network healthcare facilities may transmit locally-obtained medical images and data to the cloud (101) to be stored as remote data in the cloud repository (105) accessible to other in-network healthcare facilities. In one or more embodiments, the in-network healthcare facilities may retrieve medical images and data from the cloud (101) to be stored as local data in their respective local repositories (109).

In one or more embodiments, not all of the remote data stored in the cloud repository (105) need be retrieved by the in-network healthcare facilities to be stored as local data. The remote data to be retrieved and stored as local data may vary based on the size and need of the healthcare facility or on the preferences of the local computers (111) (e.g., healthcare professionals). For example, the remote data to be retrieved and stored as local data in the local repositories (109) of certain in-network healthcare facilities may be based on specific individuals who are patients of those facilities. Thus, if a particular individual is not a patient of a particular in-network healthcare facility, that healthcare facility may not retrieve and store that patient's medical images and data from the cloud (101) as local data. This option may be particularly useful for smaller healthcare facilities with smaller local servers (107) and local repositories (109) with limited storage and processing power. In one or more embodiments, the remote data to be retrieved and stored as local data in the local repositories (109) of certain in-network healthcare facilities may be based on a specific medical study, medical series, medical image, or medical report instead of being based on specific individuals who are patients of those facilities.

In one or more embodiments, users of the local computers (111) at each in-network healthcare facility may view the medical images and data stored on the cloud repository (105) through a web-browser based version of the application that is stored on the cloud sever (103). The user may also view the images through a local version of the application stored on the local computers (111). For example, healthcare professionals may determine if any of the local data stored in the local repository (109) has been updated by another healthcare professional associated with a different in-network healthcare facility, and retrieve the updated data from the cloud repository (105) to replace the current local data. In one or more embodiments, the updating of the local data may be performed automatically by the system (100), e.g., through the application stored on the local computers (111).

For example, an individual may be a patient at multiple in-network healthcare facilities. Each of these in-network healthcare facilities may store the individual's medical images and data as local data. In one or more embodiments, the individual's medical images and data are updated in the cloud repository (105) by one of the in-network healthcare facilities, the other in-network healthcare facilities where the individual is also a patient may automatically retrieve (synchronize) the individual's updated images and data to keep the local data in the local repository (109) up-to-date. The automatic updating of the cloud repository (105) and/or synchronization of the pertinent local repositories (109) may be triggered every time the individual's medical images or data are updated on the cloud, or may be triggered at predetermined intervals.

In one or more embodiments, medical images and data stored in the cloud repository (105) may be automatically retrieved by the local computers (111) in advance of a patient's scheduled diagnosis (i.e., a patient's appointment to receive a diagnosis). In one or more embodiments, a user at a healthcare facility where the patient's medical images and data are taken may transmit, from the local computers (111) at that healthcare facility, the medical images and data and diagnostic reservation information to the cloud server (103) to be stored in the cloud repository (105).

In one or more embodiments, a user at a different healthcare facility where the patient has a diagnosis scheduled may transmit, from the local computers (111) at that healthcare facility, an advanced-retrieval request to retrieve the patient's medical images and data that are stored on the cloud (101) in advance of the patient's scheduled diagnosis. In one or more embodiments, the advanced-retrieval request may include an advanced-retrieval time period that covers a range of a date and time of interest (e.g., 9:00 AM to 9:00 PM on Mar. 18, 2018) for retrieving medical images and data in advance of the patient's scheduled diagnosis. In one or more embodiments, the advanced-retrieval request may be automatically transmitted by the local computers periodically at a predetermined rate.

In one or more embodiments, the diagnostic reservation information includes timing information that indicates a data and time of the patient's scheduled diagnosis at the other healthcare facility and diagnosis information that includes patient information that associated (i.e., matches) the diagnostic reservation information with medical images and data stored in the cloud repository (105). The patient information that may be included in the diagnosis information are described in more detail below in reference to FIG. 3.

FIG. 1B shows an example in accordance with one or more embodiments where a connection between one of the in-network healthcare facilities and the cloud (101) is disconnected. In this state, the application may automatically configure the local computers (111) and local servers (107) at the disconnected healthcare facility to access the local data stored in the local repository (109). In one or more embodiments, the disconnected healthcare facility continues to store into the local repository (109) medical images and data taken or updated during the time of disconnection. This enables the disconnected healthcare facility to establish a continuous workflow without experiencing any downtime caused by the disconnection from the cloud (101).

Then, when the connection between the disconnected healthcare facility is reestablished with the cloud (101), the local computers (111) and local servers (107) of the reconnected healthcare facility may be configured by the application to transmit to the cloud (101) all of the medical images and data stored in the local repository taken or updated during the time of disconnection. Such medical images and data may then be stored in the cloud repository (105) as new remote data. As the cloud (101) is being updated with the medical images and data from the reconnected healthcare facility, the application stored in the local computers (111) of the other in-network facilities may automatically update their respective local repositories (109) with the new remote data.

FIGS. 2A and 2B show a display message (201) in accordance with one or more embodiments, which may be displayed as part of a pop-up window by the application on the local computer (111) for its user. In this example, the display message (201) includes a user-selectable tab (203a and 203b) (e.g., selectable by the user with a click of a mouse) and a countdown timer (205). The display message (201) may appear as a pop-up window on a display of the local computer (111). The display message (201) may contain a message related to the current connection status between the local servers (107) of the in-network healthcare facilities and the cloud server (103).

FIG. 2A shows an example of the display message (201) when the connection between a local sever (107) of one of the in-network healthcare facilities and the cloud server (103) is disconnected. The display message (201) would include a message that indicates that the connection to the cloud (101) has been disconnected and that the local computer (111) will automatically access the local repository (109) when the countdown timer (205) runs out. Although a single local repository is used in certain descriptions herein for illustration purposes, the number of local computers and local repositories at each healthcare facility may vary.

In one or more embodiments, the users operating the local computer (111) may either wait for the countdown timer (205) to run out or directly click on the user-selectable tab (203a) to access the local repository (109) instead of the cloud repository (105) (i.e., switch access to the local repository (109)).

FIG. 2B shows an example of the display message (201) when the connection between a local sever (107) of one of the disconnected in-network healthcare facility and the cloud server (103) is reestablished. The display message (201) would include a message that indicates that the connection to the cloud (101) has been reestablished and prompts the user (e.g., healthcare professional) to choose between continuing to work off the local repository (109) or to re-access the cloud repository (105). In one or more embodiments, the application of the system (100) gives the user the option to work off the local repository only temporarily (e.g., for a pre-set or predetermined time period). In such a case, as shown in the example of FIG. 2B, the display message (201) may further include a message indicating that the local computer (111) would automatically re-access the cloud repository (105) when the countdown timer (205) runs out (i.e., switch access back to the cloud repository (105)).

Still referring to FIG. 2B, in one or more embodiments, the user may either select user-selectable tab (203a) to immediately re-access the network repository (105) or select user-selectable tab (203b) to continue to work locally off the local repository (109). Again, in this example, the continued use of the local repository after the connection with the cloud has been reestablished is limited. Once the pre-set time period has expired, the user would be prompted with another display message (201) to reconnect to the cloud (101).

FIG. 3 shows an example of a data table (300) that includes data associated with each medical image. In one or more embodiments, the data table (300) may include patient related information such as, but not limited to, a Patient ID (301), Patient Name (303), Attributed Facility ID (305), Report Information (307), and Image Information (309).

In one or more embodiments, the Patient ID (301) is an individual's patient identification number. Each individual will have a single unique Patient ID (301). The individual's Patient ID (301) is shared among the in-network healthcare facilities. The Patient Name (303) is the legal name of the individual.

In one or more embodiments, the Attributed Facility ID (305) may be the identification number of the in-network healthcare facility where the individual is a patient (e.g., the in-network healthcare facility associated with the individual). If an individual frequents more than one of the multiple in-network healthcare facilities, the individual will be associated with more than one Attributed Facility ID (305). Alternatively, in one or more embodiments, the Attributed Facility ID (305) may be the identification number of the in-network healthcare facility that obtained the first image of the particular patient uploaded onto the cloud (101), in which case the patient will have no more than one Attributed Facility ID (305). In one or more embodiments, the Attributed Facility ID may be assigned directly by a user at an in-network healthcare facility (i.e., a healthcare professional).

In one or more embodiments, the Report Information (307) includes information on the individual's medical diagnosis. The Image Information (309) includes a brief description of the medical image and the name of the modality used to generate the medical image.

In one or more embodiments, the data in data table (300) is embedded as metadata in the medical image, which may be a Digital Imaging and Communications in Medicine Format (DICOM-format) image. In one or more embodiments, DICOM may be the universal image format for implementing the system (100). The data from the table (300) can be extracted from the DICOM-format images using the application of one or more embodiments stored in the local computers (111). In one or more embodiments, the data in data table (300) may also be directly imbedded as metadata in the medical data, which can be either the patient's medical images or a patient's medical report.

The data in the table (300) may be sorted in any number of ways. In the example shown FIG. 3, the data is sorted by patient. However, the data can be sorted another way using any one of the patient related information based, for example, on the preferences of the healthcare professionals. Once the data from the data table (300) has been extracted from the medical image, healthcare professionals can edit/modify the data using the GUI provided with the application of one or more embodiments. In one or more embodiments, the extracted data table (300) is stored in the local servers (107).

FIGS. 4-7 show different states of the system of FIGS. 1A and 1B in accordance with one or more embodiments. The cloud (101), the cloud server (103), the cloud repository (105), the local servers (107), the local repository (109), the local computers (111), the display message (201), the user selectable tab(s) (203a and 203b), and the countdown timer (205) may be identical or substantially similar as described above with respect to FIGS. 1A, 1B, 2A, and 2B. Detailed descriptions of such like components will not be repeated below.

Figure 4:
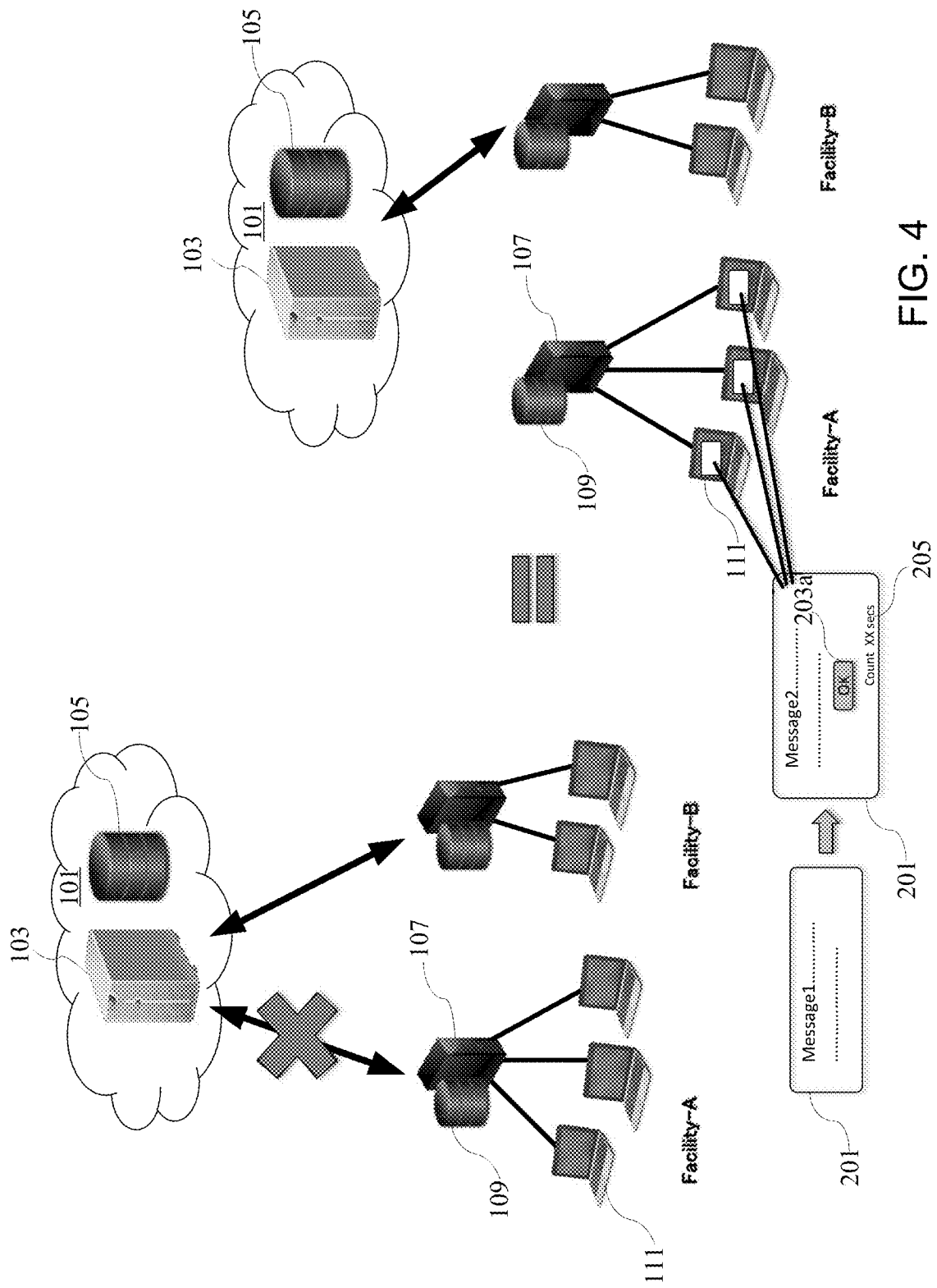
FIG. 4 shows a state of the system of FIGS. 1A and 1B in accordance with one or more embodiments.
Figure 5:
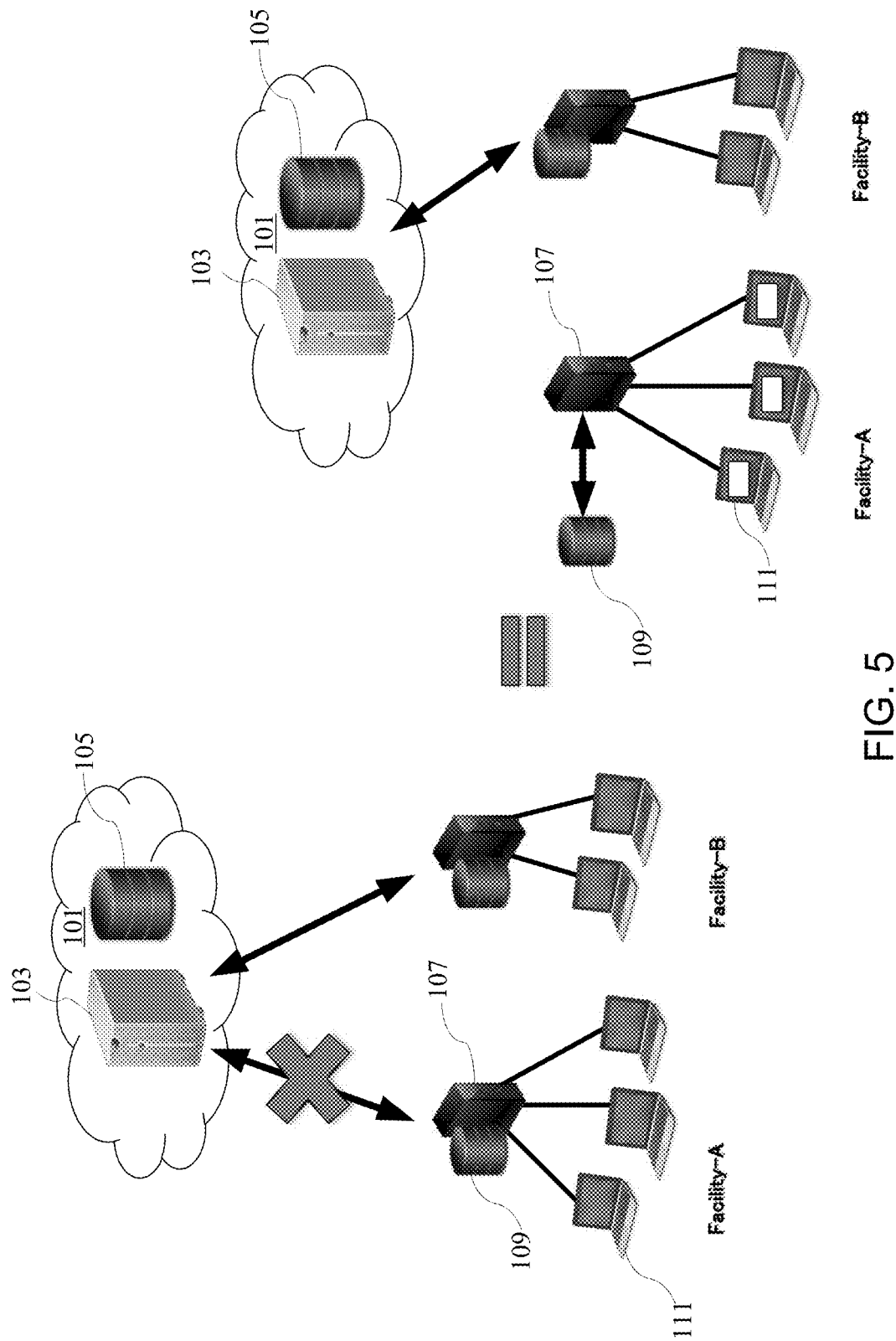
FIG. 5 shows a state of the system of FIGS. 1A and 1B in accordance with one or more embodiments.

FIGS. 4 and 5 each show a state where a connection between a healthcare facility among the multiple in-network healthcare facilities and the cloud (101) gets disconnected. In this case, as shown on the right-hand side of FIG. 4, the local computers (111) associated with the disconnected healthcare facility may first display the display message (201) to indicate that the connection to the cloud (101) is disconnected. The display message (201) may then prompt the user to switch access from the cloud repository (105) to the local repository (109) of the disconnected healthcare facility by selecting the user selectable tab (203a). Additionally or alternatively, the display message (201) may show the user the countdown timer (205) so that the switch will occur automatically once the timer has run out. The right-hand side of FIG. 5 shows the local computers (111) and local servers (107) associated with the disconnected healthcare facility has switched access from the cloud repository (105) to the local repository (109).

Figure 6:
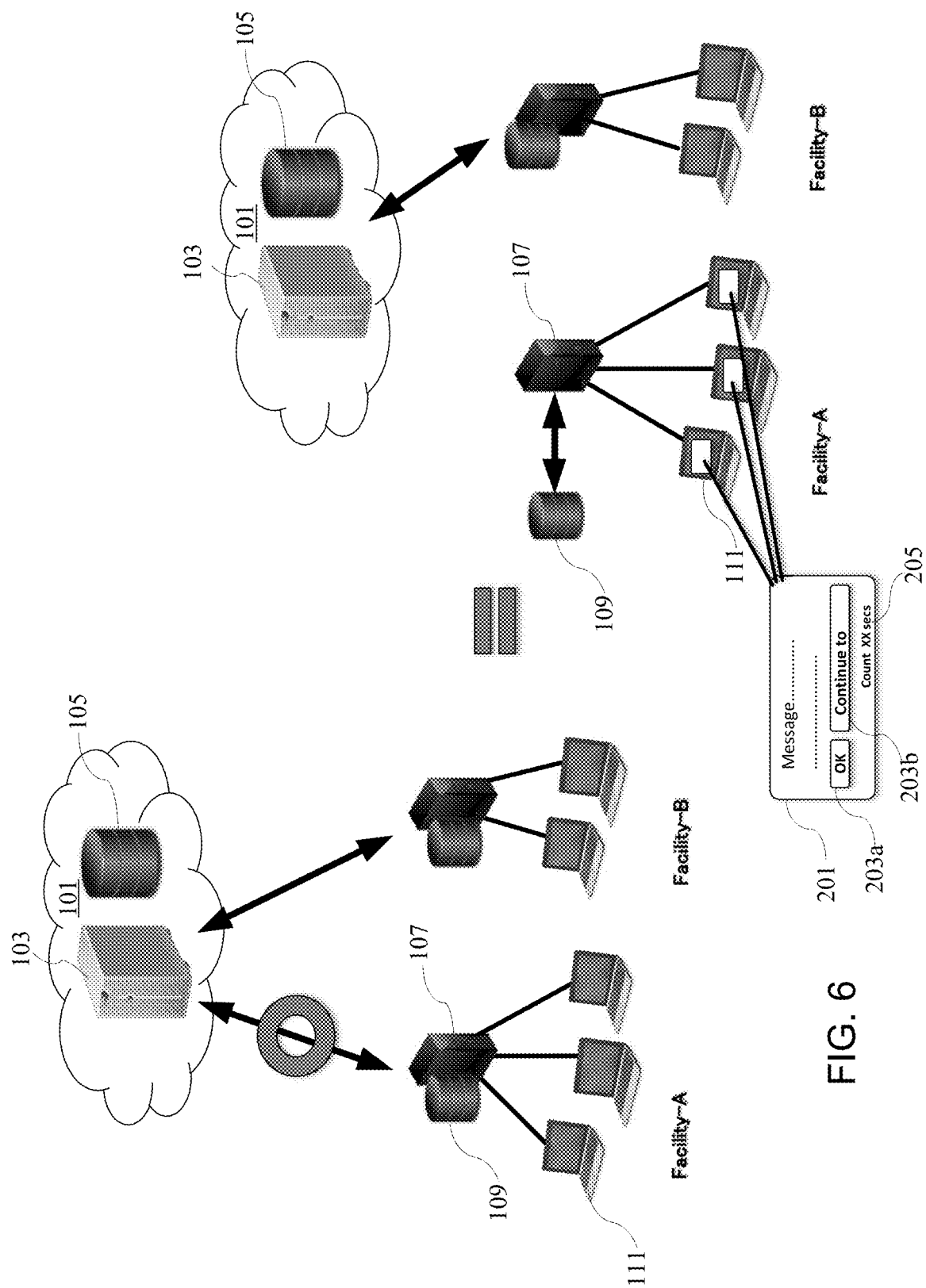
FIG. 6 shows a state of the system of FIGS. 1A and 1B in accordance with one or more embodiments.
Figure 7:
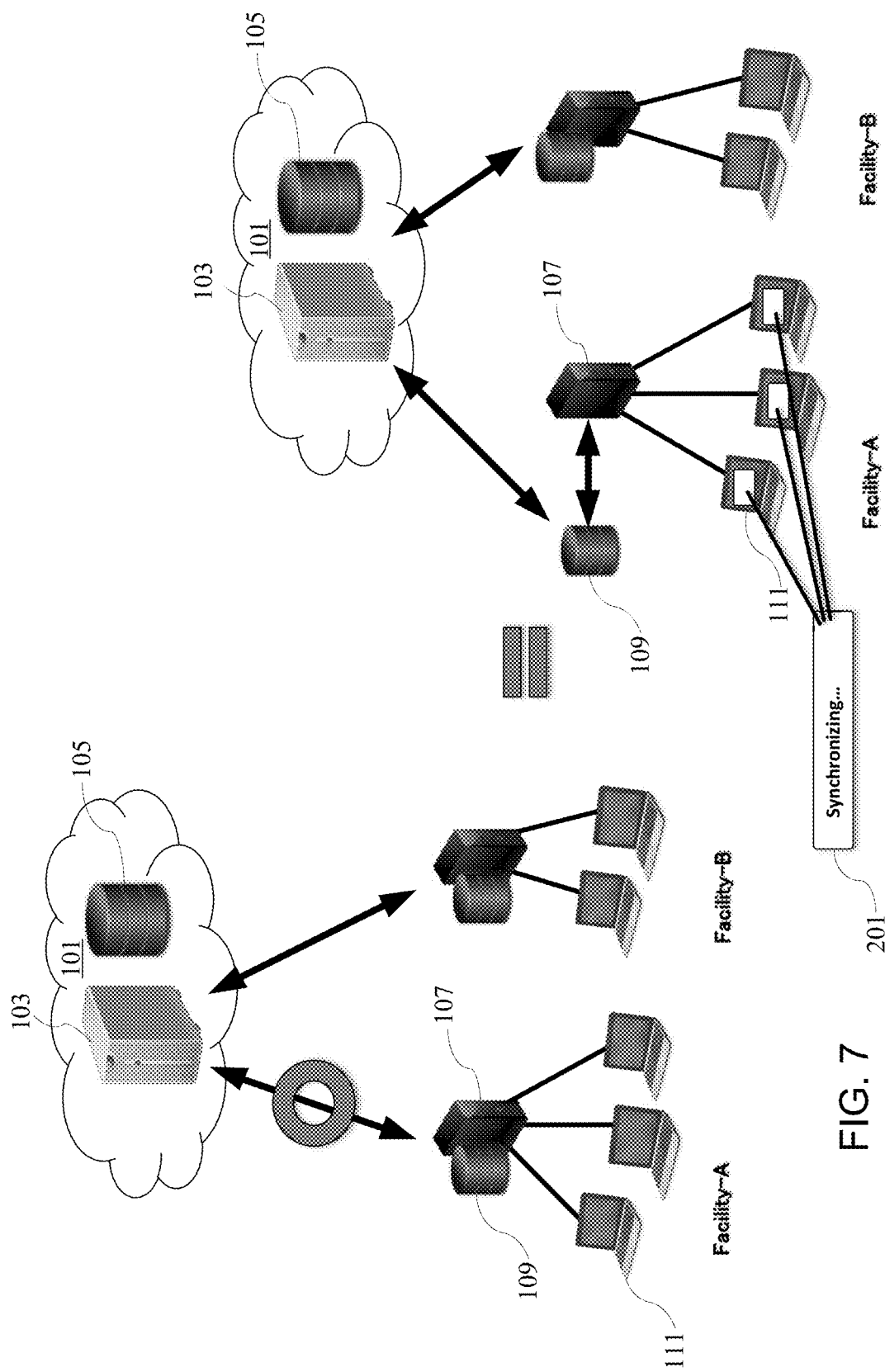
FIG. 7 shows a state of the system of FIGS. 1A and 1B in accordance with one or more embodiments.

FIGS. 6 and 7 each show a state where a connection is reestablished between the disconnected healthcare facility and the cloud (101). In this case, as shown on the right-hand side of FIG. 6, the local computers (111) associated with the re-connected healthcare facility may first display the display message (201) to indicate that the connection to the cloud (101) is re-connected. The display message (201) may then prompt the user to choose between re-accessing the cloud repository (105) (by selecting the user selectable tab (203a)) or continuing to work locally (by selecting the user selectable tab (203b)). Additionally or alternatively, the display message (201) may show the user the countdown timer (205) so that the re-accessing (i.e., switching access from the local repository (109) back to the cloud repository (105)) will occur automatically once the timer has run out. The right-hand side of FIG. 7 shows the local computers (111) associated with the re-connected healthcare facility displaying the display message (201) to indicate that the data stored in the local repository (109) during the time of disconnection is being transmitted to the cloud repository (105), and that the cloud repository (105) is synchronizing with the local repository (109).

Figure 8A:
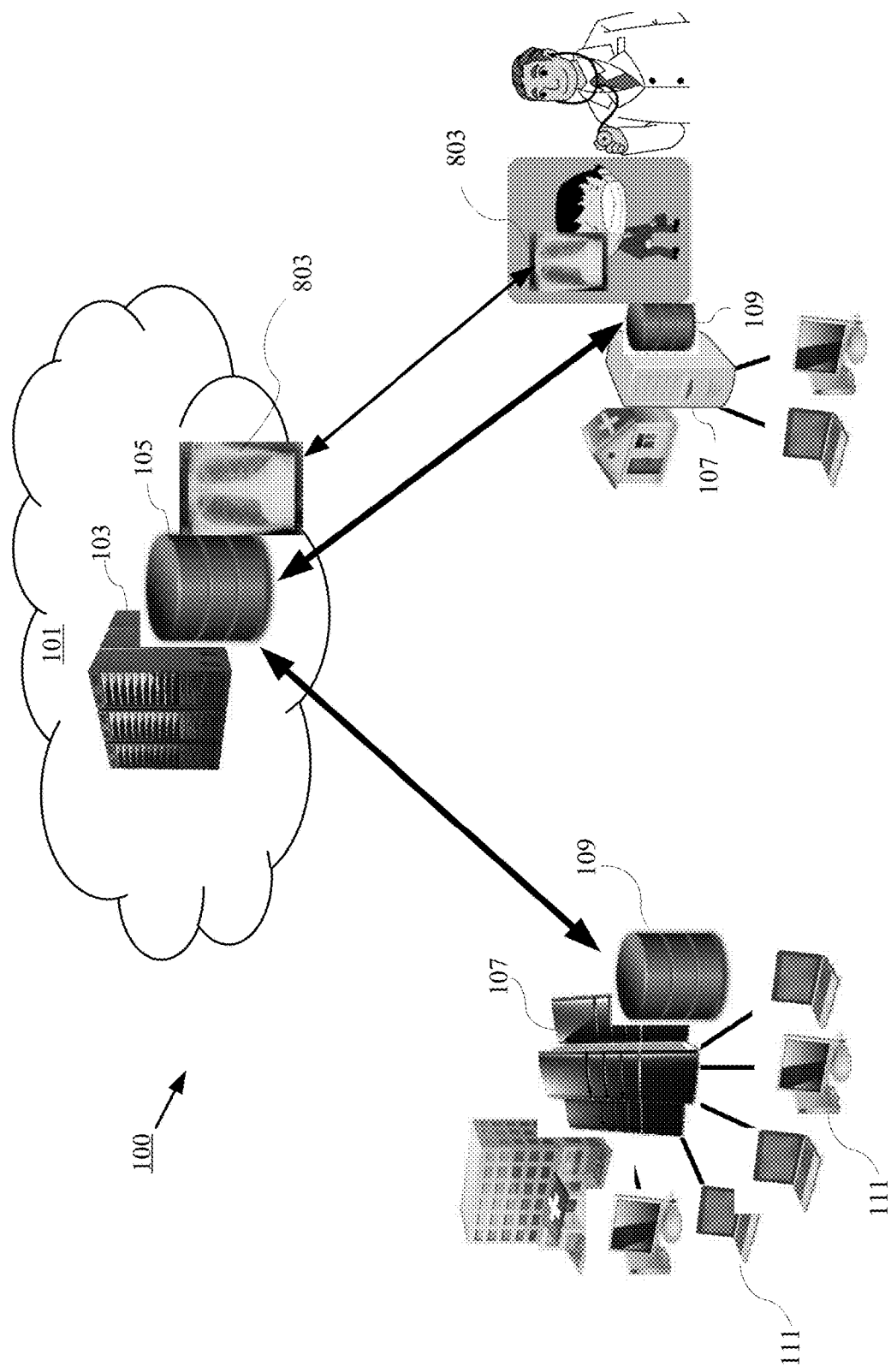
FIGS. 8A to 8C show an implementation example in accordance with one or more embodiments.
Figure 8B:
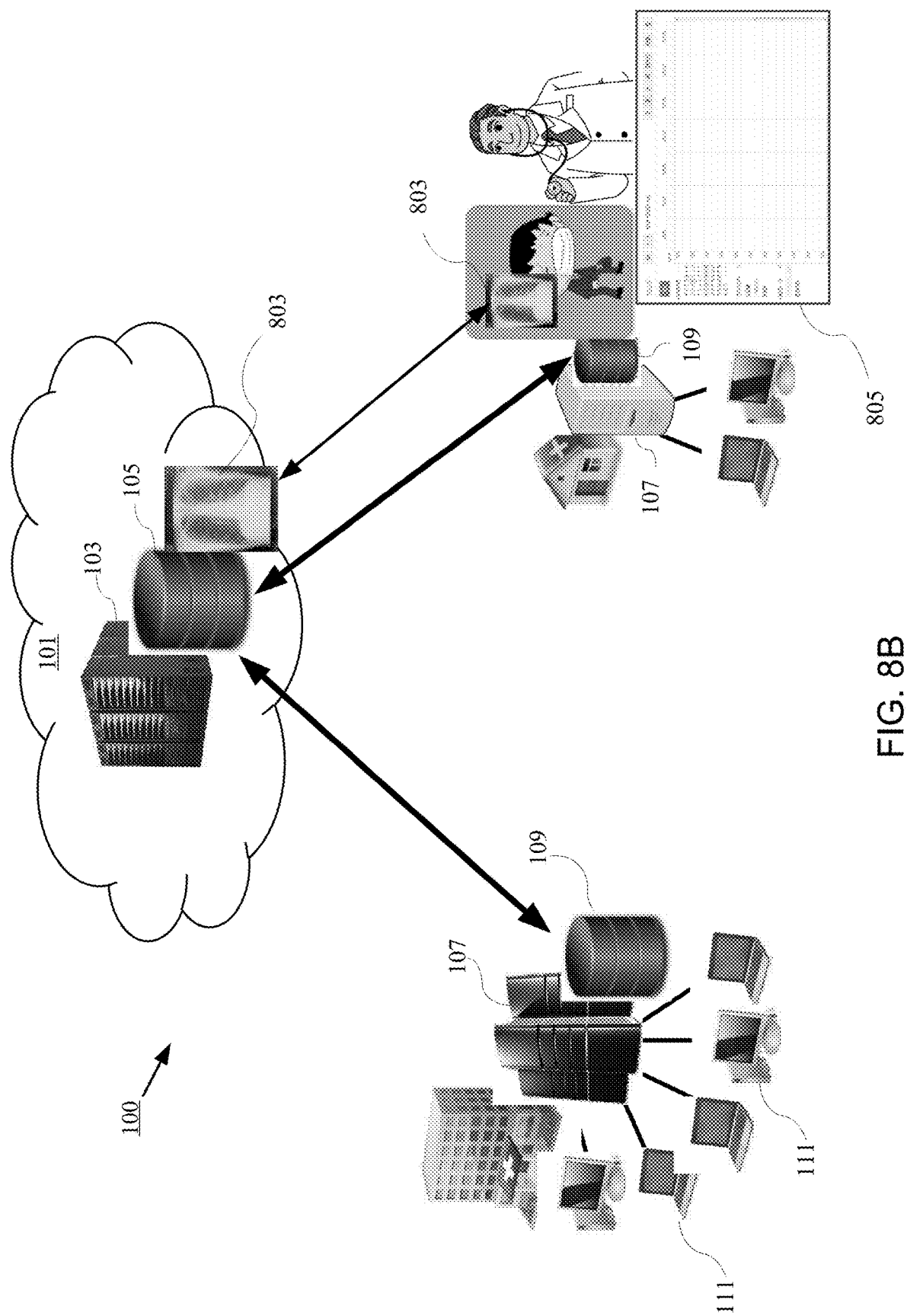
Figure 8C:
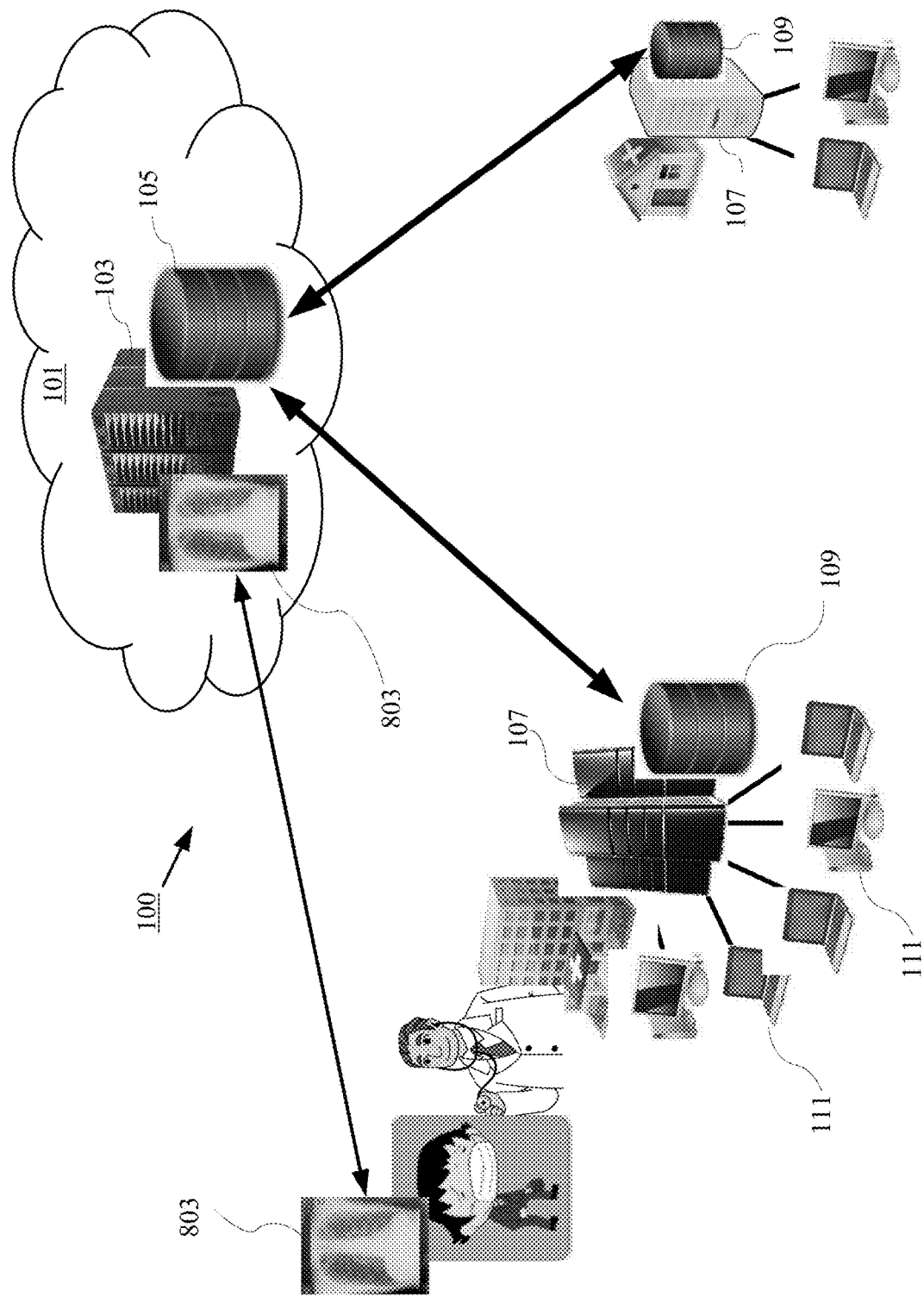

FIGS. 8A to 8C show an implementation example of an advanced retrieval of medical images and data in accordance with one or more embodiments. The implementation example of FIGS. 8A to 8C will be described with respect to system (100) as described above in reference to FIGS. 1A and 1B.

FIG. 8A shows an initial state where a patient visits a healthcare facility that is connected to the cloud-based PACS. A physician performs a diagnosis (i.e., a primary diagnosis) on the patient and locally stores a medical image (803) of the patient. The locally-stored medical image (803) of the patient is transmitted and stored in the cloud (101) when a synchronization of medical images and data between the cloud (101) and the healthcare facility occurs. In one or more embodiments, the healthcare facility initially visited by the patient may be a smaller clinic that does not have the necessary equipment to provide a complete diagnosis for the patient. The physician at the clinic may recommend the patient to visit a larger hospital, in-network hospital, to get a follow-up diagnosis (i.e., a secondary diagnosis). The physician may also help the patient schedule an appointment at the larger hospital.

FIG. 8B shows a state where the patient's diagnosis at the healthcare facility has ended. The physician at the healthcare facility may use a graphical user interface (GUI) (805) of the medical synchronization application to schedule the patient's follow-up diagnosis at the other healthcare facility (e.g., the larger hospital). In one or more embodiments, the GUI may be designed with the appearance of a calendar and the information on the calendar may be synchronized with calendar information at all other in-network healthcare facilities.

In one or more embodiments, the scheduling information entered into the GUI (805) is compiled into diagnostic reservation information that includes information about timing information on (e.g., a date and time of) the patient's next visit at the other healthcare facility and diagnosis information including the patient's ID, the patient's name, the attributed facility ID, etc. In one or more embodiments, the diagnosis information may include the information in the data table (300) as described above in reference to FIG. 3. In one or more embodiments, the diagnostic reservation information including the timing information may be stored in a metadata of the medical image (803).

FIG. 8C shows a state when the patient arrives at the other healthcare facility (e.g., the larger hospital) for the follow-up diagnosis. The local servers at the healthcare facilities periodically transmit an advanced-retrieval request to the cloud (101). In one or more embodiments, the advanced-retrieval request may include an advanced-retrieval time period that comprises a date and time range that matches (i.e., overlaps with) the timing information included in the diagnostic reservation information. In one or more embodiments, the period (i.e., predetermined rate) at which the advanced-retrieval request is transmitted to the cloud (101) may be set to any timing that would sufficiently retrieve (e.g., transmission of 2 to 3 requests per day) all medical images and data stored in the cloud (101) prior to any scheduled diagnosis associated with the medical images and data, and may be set by a user (e.g., physician, system administrator, medical staff, etc.) at each healthcare facility. Alternatively, the period may be set by the vendor of the cloud-based PACS. In one or more embodiments, based on the time of day the advanced-retrieval request is transmitted, the advanced-retrieval time period may be set differently.

In one or more embodiments, the patient's medical image (803) has been retrieved from the cloud (101) prior to the patient's arrival at the healthcare facility. This reduces the diagnosis time required by the physician because the medical image (803) is readily available in the local servers of the healthcare facility for the physician to use. In one or more embodiments, the patient's medical image (803) may be temporarily stored in the local servers of the healthcare facilities until the appointed diagnosis time.

Figure 9:
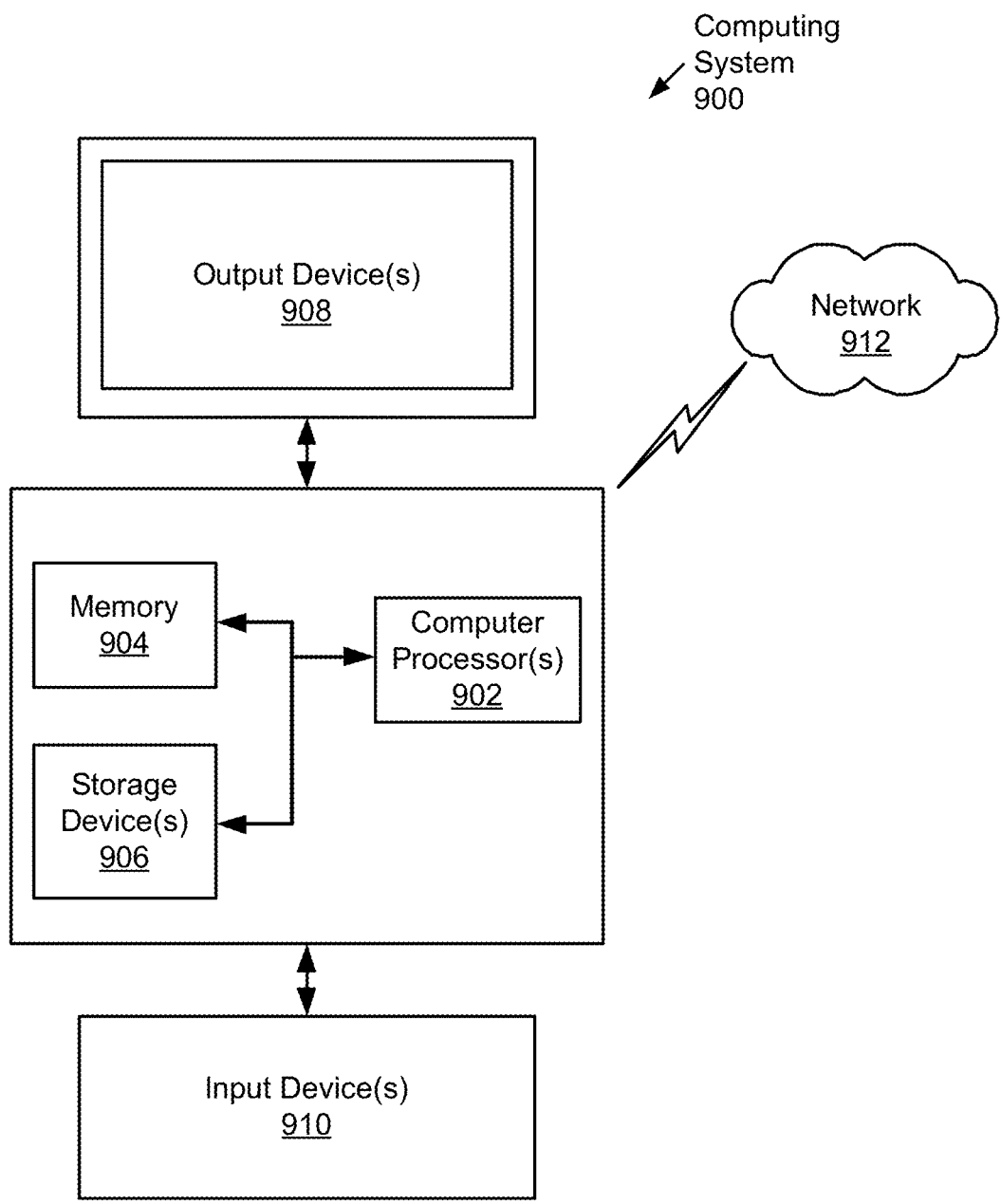
FIG. 9 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 9, the computing system (900) may include one or more computer processor(s) (902), associated memory (904) (e.g., random access memory (RAM), cache memory, flash memory, etc.), one or more storage device(s) (906) (e.g., a hard disk, an optical drive such as a compact disk (CD) drive or digital versatile disk (DVD) drive, a flash memory stick, etc.), and numerous other elements and functionalities. The computer processor(s) (902) may be an integrated circuit for processing instructions. For example, the computer processor(s) may be one or more cores, or micro-cores of a processor. The computing system (900) may also include one or more input device(s) (910), such as a touchscreen, keyboard, mouse, microphone, touchpad, electronic pen, or any other type of input device. Further, the computing system (900) may include one or more output device(s) (908), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (900) may be connected to a network (912) (e.g., a local area network (LAN), a wide area network (WAN) such as the Internet, mobile network, or any other type of network) via a network interface connection (not shown). The input and output device(s) may be locally or remotely (e.g., via the network (912)) connected to the computer processor(s) (902), memory (904), and storage device(s) (906). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (900) may be located at a remote location and connected to the other elements over a network (912). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The computing system of FIG. 9 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Figure 10:
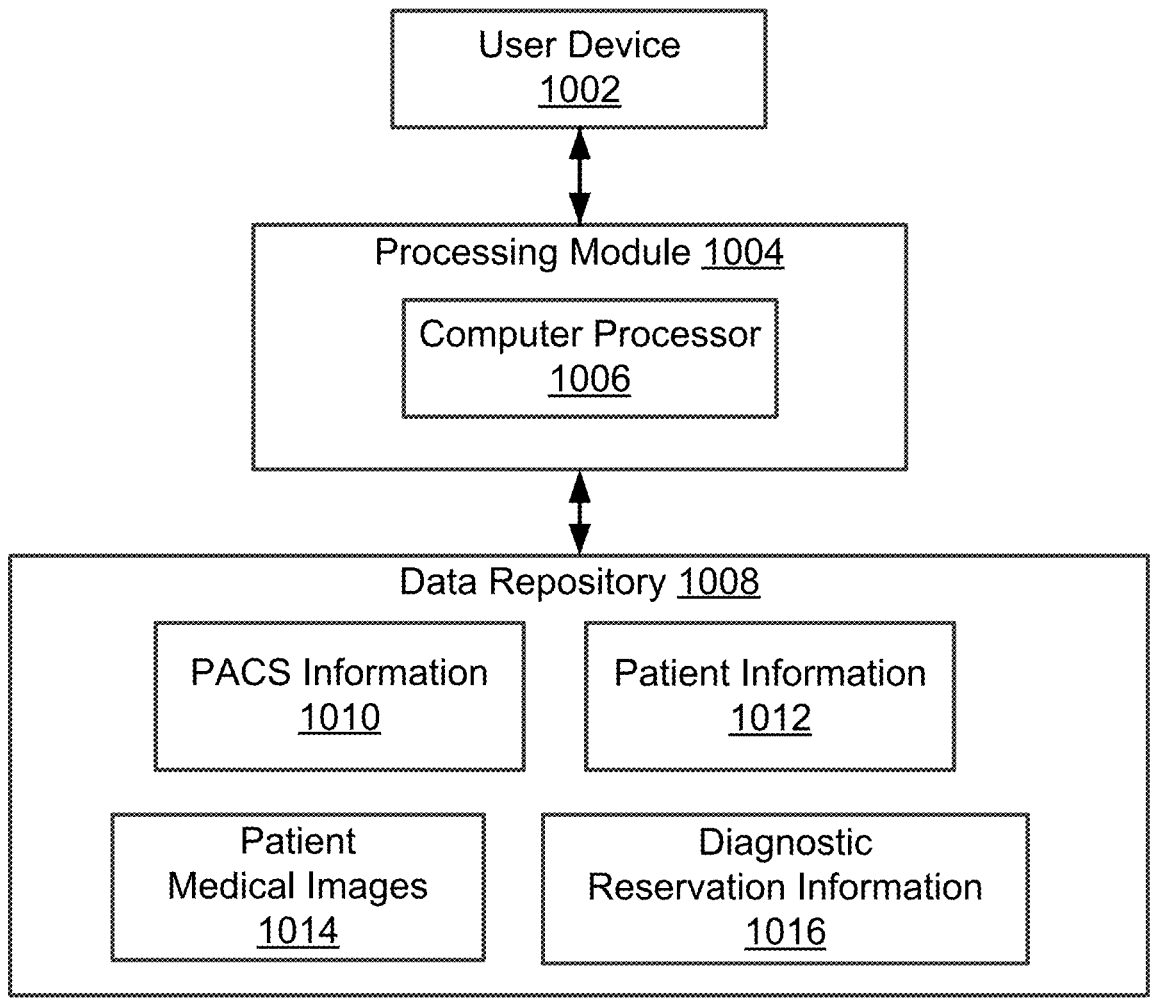
FIG. 10 shows a computing system in accordance with one or more embodiments.

FIG. 10 shows a schematic diagram of a system in accordance with one or more embodiments. The system is configured for synchronizing medical images and data between a cloud repository on a cloud server and a plurality of local repositories on a plurality of local servers connected to the cloud server. The plurality of local servers includes a first local server and a second local server and the plurality of local repositories includes a first local repository on the first local server and a second local repository on the second local server. As explained above, the use of ordinal numbers does not imply or create a particular ordering of the elements or limit any element to being only a single element. For example, the "first local server," and the "second local server," may be any local server among the plurality of local servers connected to the cloud server, and is merely called "first," and "second," for purposes of illustration.

The system as shown in FIG. 10 may include, for example, (i) a processing module (1004) including a computer processor (1006) configured to execute instructions configured to perform the following steps based on the connection status between the first local server, the second local server, and the cloud server.

In one aspect, the computer processor (1006) executes instructions to cause the cloud server to (1) receive, from the first local server at a first healthcare facility, diagnostic reservation information that includes timing information for a future diagnosis date and diagnosis information that associates the diagnostic reservation information with a medical image stored in the cloud server, (2) receive from the second local server at a second healthcare facility, an advanced-retrieval request that comprises an advanced-retrieval time period, (3) determine, in response to receiving the advanced-retrieval request, that the timing information of the diagnostic reservation information overlaps with the advanced-acquisition time period, and (4) transmitting, by the cloud server and to the second local repository in response to the medical image being associated with the diagnostic reservation information, the medical images and data.

The system as shown in FIG. 10 further comprises (ii) a user device (1002) configured to present the medical images and data to a user. The system may further include a data repository (1008) configured to store PACS application data (i.e., PACS information) (1010) related to the vendor provided application, the patient information (1012), the medical images and data (1014), and the diagnostic reservation information (1016).

Figure 11A:
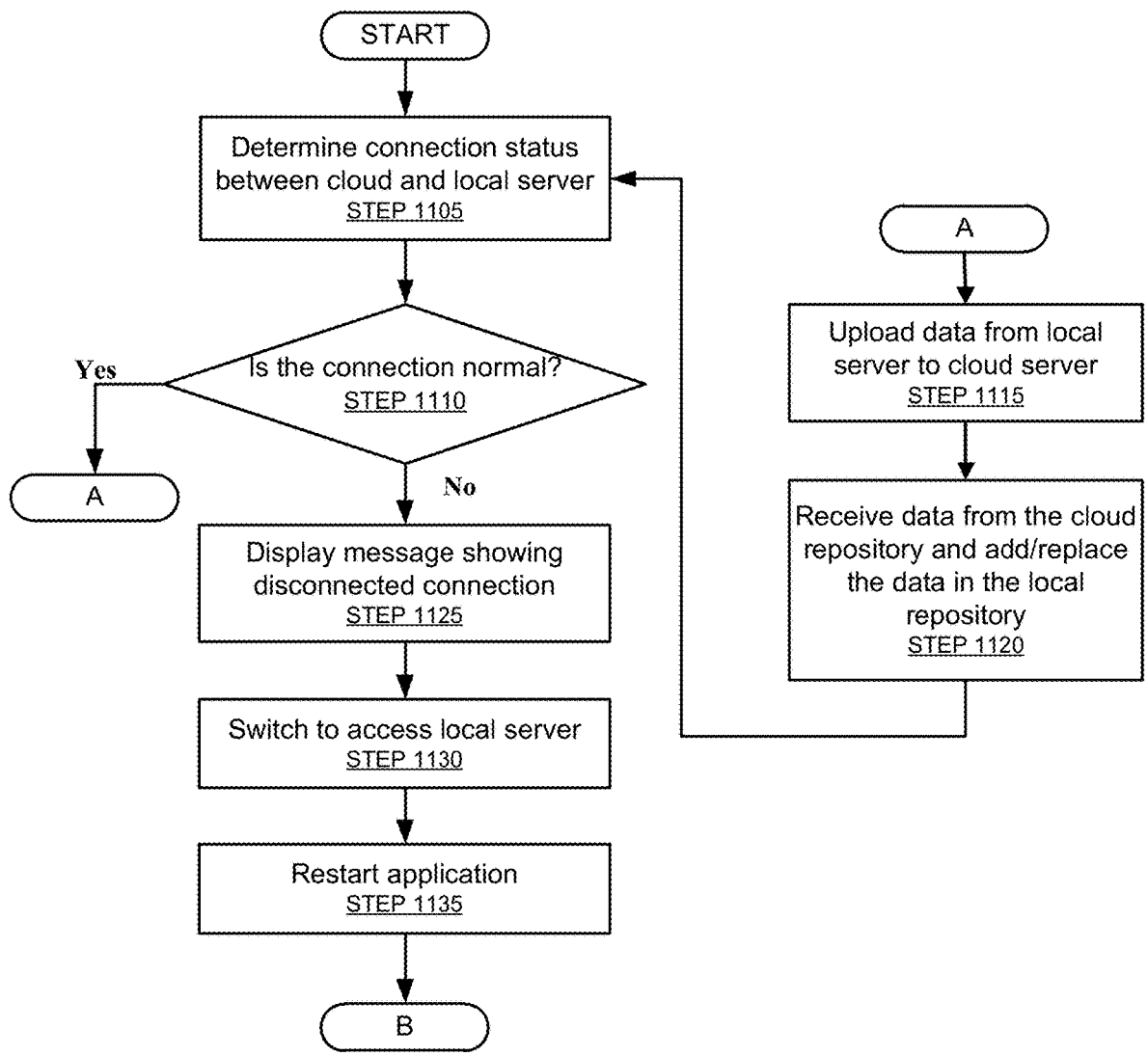
FIGS. 11A and 11B show a flowchart in accordance with one or more embodiments.
Figure 11B:
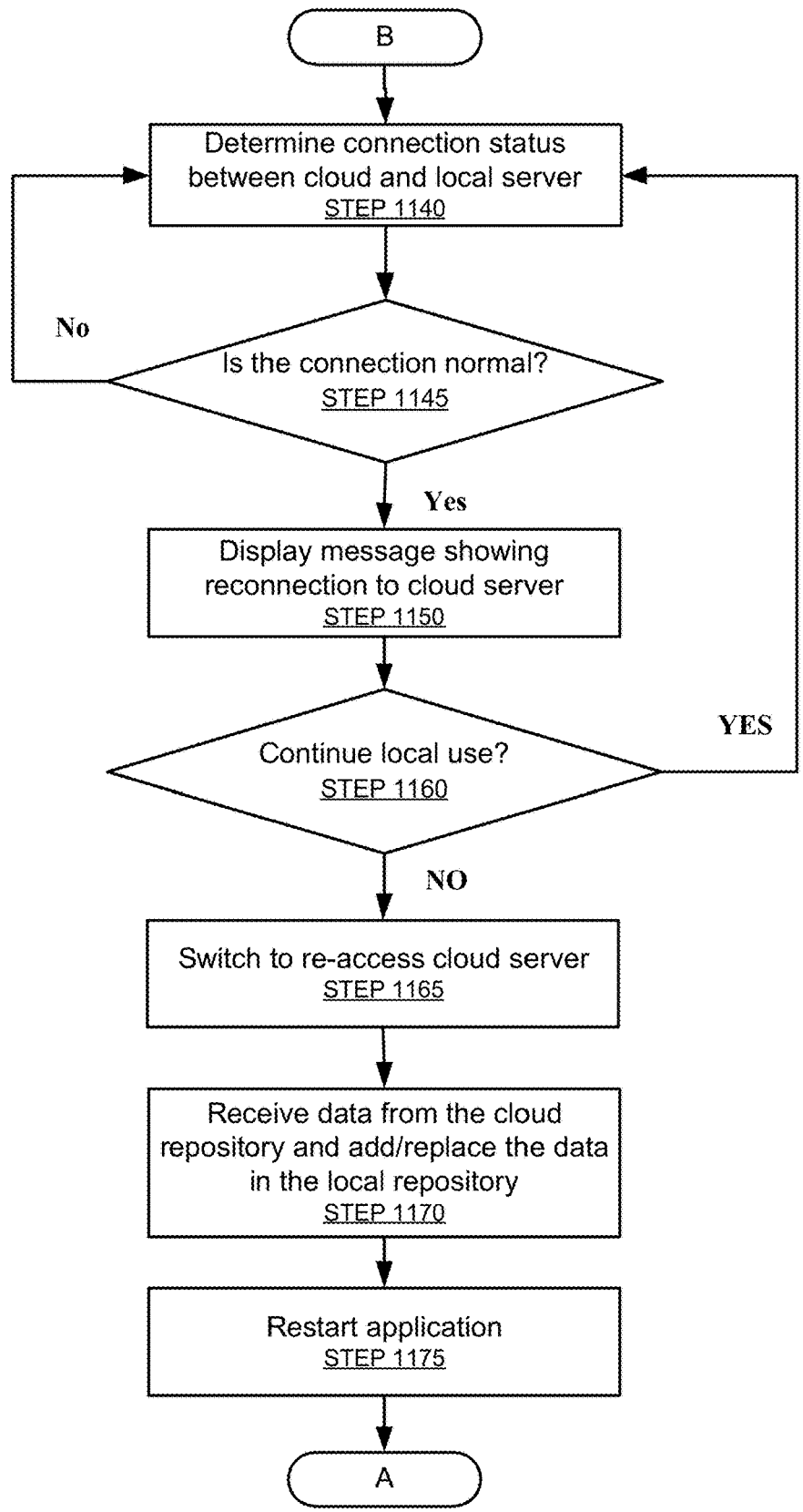

FIGS. 11A and 11B shows a flowchart of a method in accordance with one or more embodiments. In one or more embodiments, the method as shown in FIGS. 11A and 11B is a computer-implemented method. Each step shown in FIGS. 11A and 11B are described together below with respect to only a system of one healthcare facility among the multiple in-network healthcare facilities. It would be apparent to one of ordinary skill in the art that each step of the method described below can be performed by any of the systems of the multiple in-network healthcare facilities.

In Steps 1105 and 1110, the local computers associated with one of the in-network healthcare facilities check the status of the connection between the local servers of the healthcare facility and the cloud server on the cloud to determine if the connection is normal.

If the result of the check in Step 1110 is YES, the local computers continue to upload data generated by the modalities to the cloud server through the local servers in Step 1115, and synchronize a data between the local repositories and the cloud repository in Step 1120. The process then returns to Step 1105.

In one more embodiments, in response to the cloud server being updated in Step 1115, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

If the result of the check in Step 1110 is NO, a message is displayed in Step 1125 to the user indicating that the connection between the healthcare facility and the cloud is disconnected, and that the local computers and servers will be switching access to the local repository (or repositories).

In Step 1130, the local computers and servers of the disconnected healthcare facility switch access to the local repository, and, in Step 1135, an application stored on the local computers and servers that enable the local computers and servers to access the cloud is restarted. At this point, the medical images and data are being stored and retrieved from the local repository instead of from the cloud repository.

In one or more embodiments, when the message is displayed to the users, the users can either click on a user-selectable tab to instantly switch access to the local repository or wait for the local computers and servers to automatically switch access to the local repository when a countdown timer displayed on the message to run out.

In Steps 1140 and 1145, once the application has been restarted, the local computers of the disconnected healthcare facilities perform a check to determine if there is a normal connection between the local servers and the cloud server.

If the result of the check is NO, the local computers and servers continue to operate locally and the process returns to Steps 1140 and 1145 where the local computers check the status of the connection between the local server and the cloud server.

If the result of the check is YES, a message is displayed in Step 1150 to the users indicating that the connection between the healthcare facility and the cloud has been reestablished, and that the local computers and servers are switching access back to the remote repository.

In Step 1160, when the message is displayed to the users, the users are prompted to make a determination if the users want to continue to work locally off the local repository. The local computers and servers will automatically re-access the cloud server if a response by the users is not detected by the time a countdown timer on the message runs out.

If the result of the check is YES, the local computers and servers remain on the local connection for a pre-set period where the local computer continues to check the connection status between the local servers and the cloud server in Step 1140. Once the pre-set time period has expired, the user would be prompted with another display message to reconnect to the cloud. This time, the user would not be able to choose to continue to work locally off the local repository.

If the result of the check is NO, the local computers and servers are configured to re-access the cloud repository in Step 1165.

Then, in Step 1170, when the local computers and servers have re-accessed the cloud repository, the cloud repository is synchronized, i.e., updated with data stored in the local repository during the time of reconnection along with new data that was generated after the reconnection with the cloud server. In the event a conflict has occurred during the disconnection (e.g., when more than one user at different in-network healthcare facilities attempts to simultaneously update the patient information associated with the same remote data on the remote server), the conflict may be resolved automatically by the application or manually by the user through a GUI provided by the application.

In one or more embodiments, a conflict may occur when local data from the local servers of the in-network healthcare facilities are being uploaded to the cloud server (e.g., during medical data synchronization between the respective local servers and the cloud server). The conflict may occur when different users at different in-network healthcare facilities attempt to simultaneously update the same portion of the patient information of the same remote data by editing or updating the information locally in the corresponding local data. This may prevent the application from determining which of the updated patient information is correct when the cloud server tries to update the remote data using the information from the two received edited local data.

More specifically, in one or more embodiments, certain conflict situations may be more complex than others. For example, if a user at in-network healthcare facility A updates a patient name from "AAAAA" to "AAABA" and a user at a different in-network healthcare facility updates the same patient name from "AAAAA" to "AAACA," when the two users attempt to simultaneously update the same remote data to reflect the new patient name, the system will be unable to determine which of the two new names is correct. In this case, the user must manually resolve the conflict. However, if the user at in-network health care facility A edits a patient name from "AAAAA," to "AAABA," and a user at in-network healthcare facility B edits the same patient name from "AAAAA," to "ACAAA," then, when the two users attempt to simultaneously update the same remote data to reflect the new patient name, the application will be able to automatically update the patient name to "ACABA."

Further, the local computers and servers of the disconnected healthcare facility will receive data from the cloud server updated by the other in-network healthcare facilities during the time of disconnection and either add the updated data to the local repository if the updated data did not previously exist, or replace pre-existing locally-stored data that corresponds to the updated data with the updated data.

In one or more embodiments, in response to the cloud server being updated in Step 1170, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

In Step 1175, when all of the data stored in the local repository during the time of reconnection is transmitted to the cloud repository, the application is restarted and local computers are configured to return to Step 1005.

Figure 12:
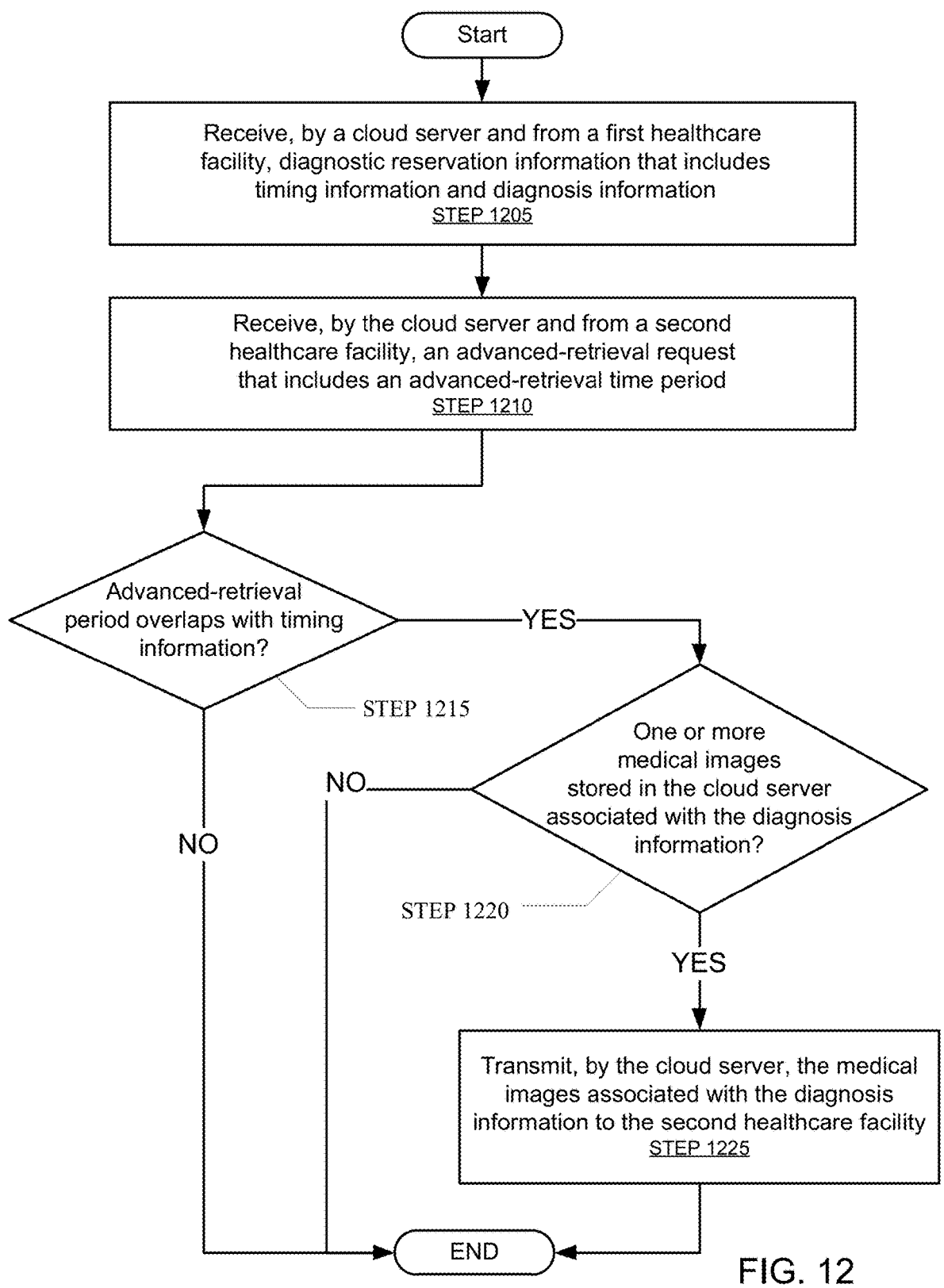
FIG. 12 shows a flowchart in accordance with one or more embodiments.

FIG. 12 shows a flowchart in accordance with one or more embodiments. Each step shown in FIG. 12 is described together below with respect to the cloud server and only systems of two healthcare facilities among the multiple in-network healthcare facilities. It would be apparent to one of ordinary skill in the art that each step of the method described below can be performed by any of the systems of the multiple in-network healthcare facilities (i.e., more than two healthcare facilities).

In STEP 1205, as described above in reference to FIGS. 1A and 1B and 8A to 8C, the cloud server receives from a first healthcare facility, diagnostic reservation information that includes timing information and diagnosis information. In one or more embodiments, the cloud server stores the diagnostic reservation information in the cloud repository. In one or more embodiments, multiple diagnostic reservation information may be stored in the cloud repository.

In STEP 1210, as described above in reference to FIGS. 1A and 1B and 8A to 8C, the cloud server receives from a second healthcare facility different from the first healthcare facility, an advanced-retrieval request that includes and advanced retrieval time period. In one or more embodiments, the advanced-retrieval request may be periodically received by the cloud server at a predetermined rate. In one or more embodiments, the cloud server may receive multiple advanced-retrieval requests from multiple in-network healthcare facilities.

In STEP 1215, described above in reference to FIGS. 1A and 1B and 8A to 8C, the cloud server determines whether the advanced-retrieval period overlaps with the timing information in the diagnostic reservation information. In the event that the advanced-retrieval period does not overlap with the timing information in the diagnostic reservation information, the advanced-retrieval process ends and nothing is transmitted to the second healthcare facility.

In STEP 1220, as described above in reference to FIGS. 1A and 1B and 8A to 8C, in the event that the advanced-retrieval period does overlap with the timing information in the diagnostic reservation information, the cloud server determines if any medical images and data stored in the cloud repository is associated with the diagnostic reservation information. The cloud server makes the determination based on the diagnosis information included in the diagnostic reservation information. In the event that the cloud server determines that no medical images and data stored in the cloud repository is associated with the diagnostic reservation information, the process ends and nothing is transmitted to the second healthcare facility.

In STEP 1225, as described above in reference to FIGS. 1A and 1B and 8A to 8C, in the event that the cloud server determines that one or more medical images and data stored in the cloud repository is associated with the diagnostic reservation information, the cloud server transmits the medical images and data to the local servers of the second healthcare facility. In one or more embodiments, the medical image and may be temporarily stored in the local servers of the second healthcare facility until a patient's appointed diagnosis time.

One or more embodiments of the invention may have one or more of the following advantages: the ability to automatically share and update medical images and data between multiple healthcare facilities that are in-network; the ability to maintain all of the local repositories of all of the in-network healthcare facilities that serve the same individual up-to-date with the individual's most recent medical images and data; the ability to establish a continuous workflow at every in-network healthcare facility without experiencing any downtime caused by a disconnection of any of the in-network healthcare facility with the share cloud; the ability to select the medical images and data to be stored in the local repositories of the respective in-network healthcare facilities so that the healthcare facilities would not need to maintain a full-sized on-site data center; the ability to reduce the time required for each patient's diagnosis by retrieving each patient's medical images and data in advance of the patient's appointed diagnosis time, which leads to more efficient use of computer resources during the diagnosis; the ability to schedule and retrieve in advance necessary medical images and data during periods when the healthcare facilities are less busy, which leads to more efficient use of computer processing resources when the healthcare facilities are busy; the ability to automatically retrieve medical images and data without a manual request, which leads to a more efficient use of personnel at healthcare facilities that are short staffed or include personnel that are overworked; etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for advanced-retrieval of medical data in a system that synchronizes medical data between a cloud repository on a cloud server and a plurality of local repositories on a plurality of local servers of healthcare facilities connected to the cloud server, wherein the healthcare facilities include at least a first healthcare facility including a first local repository and a second healthcare facility including a second local repository, the method comprising:
   detecting a disconnection between a local server of the first healthcare facility and the cloud server, wherein the local server of the first healthcare facility is configured to access the first local repository and store medical data into the first local repository while the connection is disconnected;
   detecting a reconnection between the local server of the first healthcare facility and the cloud server;
   receiving, from the local server of the first healthcare facility and in response to detecting the reconnection of the disconnected connection, the medical data stored into the first local repository during the disconnection;
   receiving, from the first healthcare facility, diagnostic reservation information, wherein the diagnostic reservation information comprises:
      timing information for a future diagnosis date of a patient at the second healthcare facility, and
      diagnosis information that associates the diagnostic reservation information with a medical image of the patient stored in the cloud server;
   receiving, from the second healthcare facility before the future diagnosis date of the patient at the second healthcare facility, an advanced-retrieval request that comprises an advanced-retrieval time period to retrieve the medical image of the patient before the future diagnosis date of the patient at the second healthcare facility, wherein the advanced-retrieval request is received at timings outside the healthcare facilities' peak patient activity that includes periods during which patient activity exceeds a predetermined threshold;
   determining, in response to receiving the advanced-retrieval request, that the timing information of the diagnostic reservation information overlaps with the advanced-retrieval time period;
   determining, in response to the timing information of the diagnostic reservation information overlapping with the advanced-retrieval time period, that the medical image is associated with the diagnostic reservation information; and
   transmitting, in response to the medical image being associated with the diagnostic reservation information, the medical image to the second local repository before the future diagnosis date of the patient at the second healthcare facility.

2. The method according to claim 1, wherein the medical image is temporarily stored in the second local repository.

3. The method according to claim 1, wherein
   the cloud server periodically receives the advanced-retrieval request from the second healthcare facility at a predetermined rate, and
   the advanced-retrieval time period is different in each of the advanced-retrieval requests.

4. The method according to claim 1, wherein the second healthcare facility is larger than the first healthcare facility.

5. The method according to claim 1, wherein:
   the first healthcare facility is where a primary diagnosis is provided,
   the second healthcare facility is where a secondary diagnosis is provided, and
   the secondary diagnosis is a follow-up of the first diagnosis.

6. The method according to claim 1, wherein each of the local servers is an application proxy server (APS) disposed in a medical facility.

7. The method according to claim 1, wherein the diagnostic reservation information is stored in a metadata of the medical image.

8. A non-transitory computer-readable medium (CRM) storing instructions that cause a cloud server coupled to a computer to perform an operation for advanced-retrieval of medical data in a system that synchronizes medical data between a cloud repository on the cloud server and a plurality of local repositories on a plurality of local servers of healthcare facilities connected to the cloud server, wherein the healthcare facilities include at least a first healthcare facility including a first local repository and a second healthcare facility including a second local repository, the operation comprising:
   detecting a disconnection between a local server of the first healthcare facility and the cloud server, wherein the local server of the first healthcare facility is configured to access the first local repository and to store medical data into the first local repository while the connection is disconnected;
   detecting a reconnection between the local server of the first healthcare facility and the cloud server;
   receiving, from the local server of the first healthcare facility and in response to detecting the reconnection of the disconnected connection, the medical data stored into the first local repository during the disconnection;
   receiving, from the first healthcare facility, diagnostic reservation information, wherein the diagnostic reservation information comprises:
      timing information for a future diagnosis date of a patient at the second healthcare facility, and
      diagnosis information that associates the diagnostic reservation information with a medical image of the patient stored in the cloud server;
   receiving, from the second healthcare facility before the future diagnosis date of the patient at the second healthcare facility, an advanced-retrieval request that comprises an advanced-retrieval time period to retrieve the medical image of the patient before the future diagnosis date of the patient at the second healthcare facility, wherein the advanced-retrieval request is received at timings outside the healthcare facilities' peak patient activity that includes periods during which patient activity exceeds a predetermined threshold;
   determining, in response to receiving the advanced-retrieval request, that the timing information of the diagnostic reservation information overlaps with the advanced-retrieval time period;

determining, in response to the timing information of the diagnostic reservation information overlapping with the advanced-retrieval time period, that the medical image is associated with the diagnostic reservation information; and transmitting, in response to the medical image being associated with the diagnostic reservation information, the medical image to the second local repository before the future diagnosis date of the patient at the second healthcare facility.

9. The CRM according to claim 8, wherein the medical image is temporarily stored in the second local repository.

10. The CRM according to claim 8, wherein
the cloud server periodically receives the advanced-retrieval request from the second healthcare facility at a predetermined rate, and
the advanced-retrieval time period is different in each of the advanced-retrieval requests.

11. The CRM according to claim 8, wherein the second healthcare facility is larger than the first healthcare facility.

12. The CRM according to claim 8, wherein:
the first healthcare facility is where a primary diagnosis is provided,
the second healthcare facility is where a secondary diagnosis is provided, and
the secondary diagnosis is a follow-up of the first diagnosis.

13. A system that synchronizes medical data, comprising:
a cloud server;
a cloud repository on the cloud server; and
a plurality of local repositories on a plurality of local servers of healthcare facilities connected to the cloud server, wherein
the healthcare facilities include at least a first healthcare facility including a first local repository and a second healthcare facility including a second local repository,
the local server of the first healthcare facility is configured to access the first local repository and to store medical data into the first local repository while a connection between a local server of the first healthcare facility and the cloud server is disconnected; and
the cloud server:
  detects a disconnection between the local server of the first healthcare facility and the cloud server;
  detects a reconnection between the local server of the first healthcare facility and the cloud server;
  receives, from the local server of the first healthcare facility and in response to detecting the reconnection of the disconnected connection, the medical data stored into the first local repository during the disconnection;
  receives, from the first healthcare facility, diagnostic reservation information, wherein the diagnostic reservation information comprises:
    timing information for a future diagnosis date of a patient at the second healthcare facility, and
    diagnosis information that associates the diagnostic reservation information with a medical image of the patient stored in the cloud server;
  receives, from the second healthcare facility before the future diagnosis date of the patient at the second healthcare facility, an advanced-retrieval request for retrieving the medical image before the future diagnosis date that comprises an advanced-retrieval time period to retrieve the medical image of the patient before the future diagnosis date of the patient at the second healthcare facility, wherein the advanced-retrieval request is received at timings outside the healthcare facilities' peak patient activity that includes periods during which patient activity exceeds a predetermined threshold;
  determines, in response to receiving the advanced-retrieval request, that the timing information of the diagnostic reservation information overlaps with the advanced-retrieval time period;
  determines, in response to the timing information of the diagnostic reservation information overlapping with the advanced-retrieval time period, that the medical image is associated with the diagnostic reservation information; and
  transmits, in response to the medical image being associated with the diagnostic reservation information, the medical image to the second local repository before the future diagnosis date of the patient at the second healthcare facility.

14. The system according to claim 13, wherein the medical image is temporarily stored in the second local repository.

15. The system according to claim 13, wherein the cloud server periodically receives the advanced-retrieval request from the second healthcare facility at a predetermined rate, and the advanced-retrieval time period is different in each of the advanced-retrieval requests.

16. The system according to claim 13, wherein the second healthcare facility is larger than the first healthcare facility.

17. The system according to claim 13, wherein:
the first healthcare facility is where a primary diagnosis is provided,
the second healthcare facility is where a secondary diagnosis is provided, and
the secondary diagnosis is a follow-up of the first diagnosis.

18. The method according to claim 1, wherein
multiple ones of the advanced-retrieval request are sent from the healthcare facilities connected to the cloud server, and
the timings that avoid peak patient activity at the healthcare facilities are set in advance so as to prevent burdening the cloud sever with the multiple ones of the advanced-retrieval request at a same time.

19. The CRM according to claim 8, wherein
multiple ones of the advanced-retrieval request are sent from the healthcare facilities connected to the cloud server, and
the timings that avoid peak patient activity at the healthcare facilities are set in advance so as to prevent burdening the cloud sever with the multiple ones of the advanced-retrieval request at a same time.

20. The system according to claim 13, wherein
multiple ones of the advanced-retrieval request are sent from the healthcare facilities connected to the cloud server, and
the timings that avoid peak patient activity at the healthcare facilities are set in advance so as to prevent burdening the cloud sever with the multiple ones of the advanced-retrieval request at a same time.

* * * * *